US00PP14410P29

(12) United States Plant Patent
Evers

(10) Patent No.: US PP14,410 P2
(45) Date of Patent: Dec. 23, 2003

(54) HYBRID TEA ROSE PLANT NAMED 'TAN98485'

(50) Latin Name: *Rosa hybrida*
Varietal Denomination: TAN98485

(75) Inventor: Hans-Jürgen Evers, Uetersen (DE)

(73) Assignee: Rosen Tantau Mathias Tantau Nachfolger, Uetersen (DE)

( * ) Notice: Subject to any disclaimer, the term of this patent is extended or adjusted under 35 U.S.C. 154(b) by 0 days.

(21) Appl. No.: 10/368,042

(22) Filed: Feb. 13, 2003

(51) Int. Cl.[7] ..... A01H 5/00
(52) U.S. Cl. ..... Plt./130
(58) Field of Search ..... Plt./130

*Primary Examiner*—Bruce R. Campell
*Assistant Examiner*—Annette H. Para
(74) *Attorney, Agent, or Firm*—Klarquist Sparkman, LLP

(57) ABSTRACT

Hybrid tea rose plant having large, silvery-blue, fragrant flowers.

1 Drawing Sheet

Genus and species: Rosa hybrida.
Varietal denomination: 'TAN98485'.

SUMMARY OF THE INVENTION

The present invention relates to a new and distinct variety of hybrid tea rose plant named 'TAN98485', which was originated by me by crossing two unnamed, unpatented varieties.

BACKGROUND OF THE INVENTION

The primary objective of this breeding was to produce a new rose variety having large, silvery-blue, fragrant flowers.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Fragrance;
2. Large flowers; and
3. Bluish petals.

Asexual reproduction of this new variety by budding on *Rosa canina* rootstock, as performed at Uetersen, Germany, shows that the foregoing and all other characteristics and distinctions come true to form and are established and transmitted through succeeding propagations.

COMPARISON WITH PARENTS

'TAN98485' bears blossoms of a lilac color. The female parent has bluish-pink flowers; the male parent has pink flowers.

COMPARISON WITH SIMILAR VARIETY

The variety Mainzer Fastnacht (unpatented) is the most similar variety and is more perfumed than the candidate variety.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—Unnamed variety.
*Pollen parent.*—Unnamed variety.

FLOWER

Observations made from plants of 22 months of age grown in a greenhouse environment at Uetersen, Germany.

Blooming habit: Continuous.
Bud:
*Size.*—About 6 cm long and 4 cm in diameter long when the petals start to unfurl.
*Form.*—The bud form is globular.
*Color.*—When sepals first divide, bud color is Red-Purple Group 74B. When half blown, the upper sides of the petals are Red Group 74D; and the lower sides of the petals are Red Group 74C.
*Sepals.*—Color: Green Group 143A. Upper surface: Green Group 143B. Lower surface: Green Group 143A. Length: 3 cm. Width: 0.8 cm. Shape: Triangular. Surface texture: Smooth. There are five lightly appendaged sepals. There are unappendaged sepals with smooth edges.
*Receptacle.*—Color: Green Group 143A. Shape: Funnel. Size: 1.1 cm in diameter.
*Peduncle.*—Length: Medium, averaging about 7 cm. Surface: Smooth. Color: Green Group 143B. Strength: Erect.

Bloom:

*Size.*—Average open diameter is about 8 cm.

*Borne.*—Singly.

*Stems.*—Strength: Strong. Average length is about 68 cm and 0.3 cm in diameter.

*Form.*—When first open: Globular. Permanence: Outer petal edges curl slightly.

*Petalage.*—Number of petals under normal conditions: 31.

*Color.*—The upper sides of the petals are Red-Purple Group 74C. The reverse sides of the petals are bluish-pink near Red-Purple Group 74D. The base of each petal has a bright spot of Red-Purple Group 69D. The major color on the upper side is bluish-pink near Red-Purple Group 74C. All petals have bright sap veins.

*Variegations.*—None.

*Discoloration.*—The general tonality at the end of the first day: No change. At the end of the third day: Color fades to Red-Purple Group 71C.

*Fragrance.*—Strong, sweet.

Petals:

*Texture.*—Leathery.

*Surface.*—Smooth.

*Shape.*—Oval.

*Size.*—Width: 4 cm. Length: 4.2 cm.

*Margin.*—Smooth, not serrated. Apex Shape: Blunt. Base Shape: Cordate.

*Form.*—Flat, edges slightly quilled.

*Arrangement.*—Irregular.

*Petaloids.*—Number: 5. Color: Red-Purple Group 74C and Red-Purple Group 74D.

*Persistence.*—Petals hang on and dry.

*Lastingness.*—On the plant: about 10–12 days. As a cut flower: Fair (about 11 days).

Reproductive parts:

*Stamens.*—Number: 91. Length: 0.4 cm. Anthers: Length: 0.2 cm. Color: Brown Group 200B. Arrangement: Regular around styles. Filaments: Color: Greyed-Yellow Group 160A. Length: 0.3 cm. Pollen: Color: Greyed-Orange Group 168A.

*Pistils.*—Number: 58. Length: 0.6 cm. Styles: Color: Yellow-White Group 158A. Length: 0.4 cm. Stigmas: Color: Orange-White Group 159A. Length: 0.4 cm.

*Hips.*—None produced.

PLANT

*Form.*—Bush.

*Growth.*—Vigorous.

*Mature plant.*—Height: 90 cm. at three years. Width: 3 cm.

*Rootstock.*—*Rosa canina.*

Foliage: Number of leaflets on normal mid-stem leaves: 7.

*Size.*—Large (16.4 cm long×8.5 cm wide).

*Quantity.*—Normal.

*Color.*—New foliage: Upper side: Green Group 139B. Lower side: Green Group 139C. Old foliage: Upper side: Green Group 136B. Lower side: Green Group 136C.

Leaflets:

*Size.*—About 6 cm long×4 cm wide.

*Shape.*—Pointed oval.

*Base shape.*—Blunt.

*Apex shape.*—Pointed.

*Texture.*—Upper side: Leathery.

*Edge.*—Serrated.

*Serrations.*—Single.

*Petiole.*—Color: Green Group 139B.

*Petiole rachis.*—Color: Green Group 139D. Underside: Smooth.

*Stipules.*—Smooth. Length: 1.7 cm.

*Disease resistance.*—No information available yet. Not tested.

*Pest persistence.*—No information available yet. Not tested.

*Vein color.*—Green Group 139D.

*Venation pattern.*—Symmetrical web.

Wood:

*New wood.*—Color: Green Group 139B. Bark: Smooth.

*Old wood.*—Color: Greyed-Orange Group 177A. Bark: Rough.

Prickles:

*Quantity.*—On main canes from base: 3 per internode. On laterals from main canes: 3 per internode.

*Form.*—Hooked downward.

*Length.*—0.4 cm.

*Color when young.*—Greyed-Red Group 181A.

*Color when mature.*—Greyed-Orange Group 177A.

Small prickles:

*Quantiy.*—On main stalks: None. On laterals: None.

Winter hardiness: Not tested.

I claim:

1. A new and distinct variety of rose plant of the hybrid tea class, substantially as herein shown and described, characterized particularly by its large, silvery-blue, fragrant flowers.

* * * * *

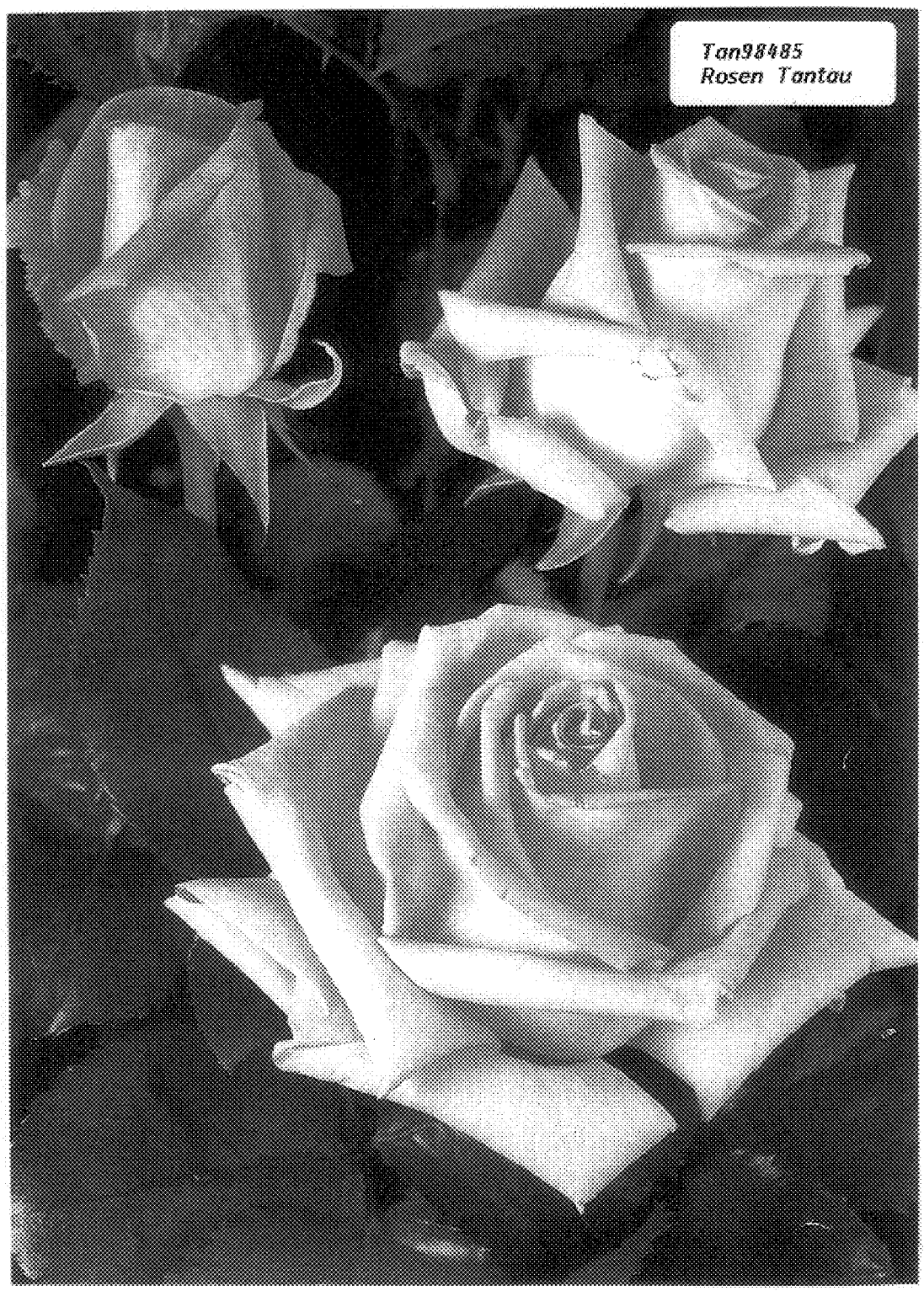
Tan98485
Rosen Tantau